(12) United States Patent
Honigs et al.

(10) Patent No.: US 6,477,392 B1
(45) Date of Patent: Nov. 5, 2002

(54) CALIBRATION OF NEAR INFRARED QUANTITATIVE MEASUREMENT DEVICE USING OPTICAL MEASUREMENT CROSS-PRODUCTS

(75) Inventors: David E. Honigs, Hagerstown, MD (US); Robert D. Rosenthal, Montgomery Village, MD (US)

(73) Assignee: Futrex Inc., Gaithersburg, MD (US)

( * ) Notice: Subject to any disclaimer, the term of this patent is extended or adjusted under 35 U.S.C. 154(b) by 4 days.

(21) Appl. No.: 09/617,046

(22) Filed: Jul. 14, 2000

(51) Int. Cl.[7] ................................................. A61B 5/00
(52) U.S. Cl. ........................ 600/316; 600/365; 600/322
(58) Field of Search ............................... 600/309–310, 600/322–324, 319, 316, 331, 365; 356/39–42

(56) References Cited

U.S. PATENT DOCUMENTS

| | | | |
|---|---|---|---|
| 4,286,327 A | | 8/1981 | Rosenthal et al. |
| 4,883,953 A | * | 11/1989 | Koashi et al. ......... 250/339.09 |
| 5,028,787 A | | 7/1991 | Rosenthal et al. |
| 5,077,476 A | | 12/1991 | Rosenthal |
| 5,313,941 A | * | 5/1994 | Braig et al. ................. 600/322 |
| 5,452,723 A | * | 9/1995 | Wu et al. .................... 600/342 |
| 5,606,164 A | * | 2/1997 | Price et al. ............ 250/339.09 |
| 5,752,512 A | * | 5/1998 | Gozani ....................... 600/347 |

* cited by examiner

*Primary Examiner*—Eric F. Winakur
*Assistant Examiner*—Matthew Kremer
(74) *Attorney, Agent, or Firm*—Rothwell, Figg, Ernst & Manbeck

(57) ABSTRACT

In a method to improve the calibration of a non-invasive, near infrared (NIR) measurement device, a plurality of data terms is formed for the NIR measurement device. Then the codependence of the data terms is evaluated by forming cross-products terms using the data terms. Next, sets of prespecified sizes are randomly formed from the data terms and the cross-product terms. Each of these sets of terms is evaluated by testing the ability of the set to predict a set of accurate measurements using regression analysis. The method then selects one of the sets based on preselected criteria and uses the selected set to calibrate the NIR measurement device.

17 Claims, 6 Drawing Sheets

CALIBRATION OF NEAR INFRARED QUANTITATIVE MEASUREMENT DEVICE USING OPTICAL MEASUREMENT CROSS-PRODUCTS

FIELD OF THE INVENTION

The present invention relates to instruments for the non-invasive quantitative measurement of constituents, such as blood glucose levels in blood. More specifically, this invention provides improvements in methods and apparatus for near-infrared quantitative analysis.

BACKGROUND AND RELATED PRIOR ART

The use of quantitative near-infrared ("NIR") analysis for the determination of chemical and/or physical characteristics of products is relatively well known in the art. See "An Introduction to Near Infrared Quantitative Analysis,"by Robert D. Rosenthal, presented at the 1977 Annual Meeting of the American Association of Cereal Chemists, (1978). See also U.S. Pat. No. 4,286,327 issued to Rosenthal et al. on Aug. 25, 1981.

Another well-known application of NIR analysis relates to the quantitative measurement of analytes in mammals, such as quantitative analysis of glucose in the blood. Information concerning the chemical composition of blood is widely used to assess the health characteristics of both people and animals. More specifically, analysis of the glucose content of blood provides an indication of the current status of the metabolism. Blood analysis, by the detection of above or below normal levels of various substances, also provides a direct indication of the presence of certain types of diseases and dysfunctions.

In particular, the non-invasive NIR quantitative measurement apparatus has particular application for use by diabetics in monitoring the level of glucose in the blood. See U.S. Pat. No. 5,028,787, Rosenthal et al., issued Jul. 2, 1991, the subject matter of which is hereby incorporated by reference in its entirety.

Quantitative NIR analysis is based on the principle that most organic (and some inorganic) substances absorb radiation in the near-infrared range, with the different substances having different absorption characteristics over specific NIR wavelength ranges. These different characteristics are then used to formulate specific measurement algorithms for obtaining quantitative information regarding the presence of such substances in the subject sample, product or patient.

The above-cited '327 patent teaches the use of infrared emitting diodes (IREDs) as sources of near-infrared radiation. As shown in FIG. 1, a plurality (eight in the figure) of IREDs 10 is arranged over a sample WS to be illuminated for quantitative analysis. Near-infrared radiation emitted from each IRED impinges upon an accompanying optical filter 12. Each optical filter 12 is a narrow bandpass filter that passes NIR radiation at a different wavelength, and light baffles 14 are provided between IREDs to prevent an IRED's light from being transmitted through an adjacent filter. In the illustrated example, the sample WS is held in a holder 16 having a transparent bottom 18. NIR radiation passing through the sample and the holder is detected by a detector 20, such as a silicon photodetector, and converted to an electrical signal. The electrical signal is processed by processing circuitry, including an amplifier 22, logarithmic amplifier 23, and analog-to-digital converter 24, and inputted to microprocessor 11. The microprocessor processes the data from the detector, using preprogrammed algorithms to obtain a quantitative measurement of the analytes of interest in the sample, and outputs the result on a display 26.

FIG. 2 illustrates another known NIR instrument for non-invasive measurement of blood analytes, as disclosed in U.S. Pat. No. 5,077,476, issued to Rosenthal on Dec. 31, 1991. The subject matter of the '476 patent is also incorporated by reference herein in its entirety. In brief summary, the instrument 1 uses a number of IREDs (50, 60 as shown in FIG. 2) for irradiating a body part, such as the finger, with NIR radiation at selected wavelengths. Narrow bandpass optical filters 160 and 170 are positioned at the output of the IREDs to pass NIR radiation at a selected wavelength. The radiation passes through a window 140, through the subject, and is detected by a detector 80. A light baffle 40 is provided to isolate the various IREDs to prevent radiation from one IRED passing through the optical filter associated with a different IRED.

The detector 80 outputs a signal to a microprocessor 100 through amplifier 90. The microprocessor calculates the concentration of analytes at issue (such as blood glucose) using preprogrammed algorithms and outputs the results to a display device 180. In this instrument, timing and control circuitry 110 is provided to sequentially and individually turn on and off each IRED, one at a time, so that the absorption by the blood analytes and other substances may be measured at each particular wavelength specified in the measurement algorithm.

In almost all known NIR measurement devices, such as those described above, the preprogrammed algorithms for interpreting the quantitative measurements are based upon Beer's Law, which provides that the amount of chemical constituent(s) to be measured is linearly related to D, where $$D = \log\left(\frac{1}{I}\right), \tag{Equation 1}$$

in which I can be the fraction of light that is either transmitted through an object, reflected off an object or interacted with the object. This linear concept has worked quite well in many NIR measurement applications. For example, U.S. Pat. No. 4,928,014, issued May 22, 1990 to Rosenthal, provides for the measurement of body fat in the human body using an NIR measurement device.

These historical successes using Beer's Law have been in applications where the change in constituent concentration has been modest. For example, in the measurement of body fat, as taught by the '014 patent, the percentage of body fat varies from a minimum in the neighborhood of 10% to a maximum of approximately 40%, a four to one change. In contrast, a much larger range of concentration change occurs in certain blood analytes. For example, blood glucose molality can vary from 20 mg/dL to more than 500 mg/dL, a change of twenty-five to one. Over such large ranges of values, the basic assumption in Beer's Law of linearity may be invalid. As a result, conventional Multiple Linear Regression ("MLR") or factor analysis does not provide sufficient accuracy to be meaningful. In fact, the D values, as defined in Equation 1, from the NIR measurement of blood glucose values generally have a highly nonlinear relationship.

Attempts to use an NIR device to measure blood glucose have encountered many problems. The NIR measurement devices must be calibrated for each individual user, with more accurate calibrations resulting in more accurate readings. It is generally tedious and time consuming to accurately calibrate the NIR measurement device. During the calibration, measurements of the NIR device are compared with other measurements known to be accurate. The NIR device is then adjusted to produce measurements that correspond with the measurements known to be accurate. The conventional approach for the NIR calibration is to evaluate absorption wavelengths and reference wavelengths. The absorption wavelengths are the portions of the electromagnetic spectrum with high absorbance due to the particular constituents of interest, and reference wavelengths are the portions of the spectrum that are insensitive to the particular constituents. However, in the very near infrared portion of the spectrum, from 700 nm to 1100 nm, the absorptions are quite broad, and thus, independent selection of wavelengths is difficult. Moreover, in the case of in vivo measurement of various blood analytes through a body part, the problem is even more difficult. Approximately ninety-nine percent of the organic content of a finger is due to the presence of water, fat and muscle (protein). The remaining 1 percent includes all of the blood analytes to be measured, as well as other materials. Even further complicating the NIR measurement is that blood analytes, such as blood glucose, are very weak NIR absorbers. There thus exists the overall challenge of measuring a very minute quantity of a substance that is a weak absorber in the presence of very strong absorbers in a portion of the spectrum where individual absorption characteristics are not easily recognizable.

Thus, there presently exists a need for an improved methodology to produce an accurate NIR measurement over a large range of possible values. Furthermore, the methodology needs to allow for the calibration of an NIR instrument to achieve the accurate, non-invasive measurement of blood analytes, especially weak absorbers such as blood glucose.

Accordingly, there is further need for a methodology that is able to calibrate an NIR blood glucose measurement unit so that the calibration is usable over a wide range of values. More specifically, the methodology needs to be accurate at the low and high glucose values so that NIR measurement device is of value in diagnosing and preventing hypoglycemia and hyperglycemia. The methodology needs to provide sufficient accuracy for medical use, so the method should provide a calibration that produces accuracy at least equal to the home finger stick meters used during the Diabetes Control and Complications Trial (DCCT). Furthermore, the methodology needs to produce a calibration that is robust and, therefore, able to accurately predict blood glucose over a reasonably extended period of time and to minimize the need for recalibration.

SUMMARY OF THE INVENTION

In response to these needs, the present invention provides a method that better analyzes the near infrared ("NIR") measurement data terms to achieve a better calibration of the NIR measurement device to the specific user. The method uses the codependence of data to extract additional information from the NIR measurement device. Codependence of the data terms is represented in cross-product terms. The cross-product terms are formed in the first step of the method by using the data terms from the NIR measurement device. Then in the second step, statistical analysis is performed using the data terms and the cross-product terms to find a desirable calibration. During this second step, randomly generated sets of the data terms and the cross-product terms are tested to find a best solution, according to prespecified conditions. More specifically, the invention includes a means to select randomly a desirable combination of data and cross-product terms to produce a good calibration to improve the predictability of blood analyte measurements.

BRIEF DESCRIPTION OF THE DRAWINGS

The invention will be described in detail with reference to the following drawings in which.

DETAILED DESCRIPTION OF THE PREFERRED EMBODIMENTS

Figure 1:
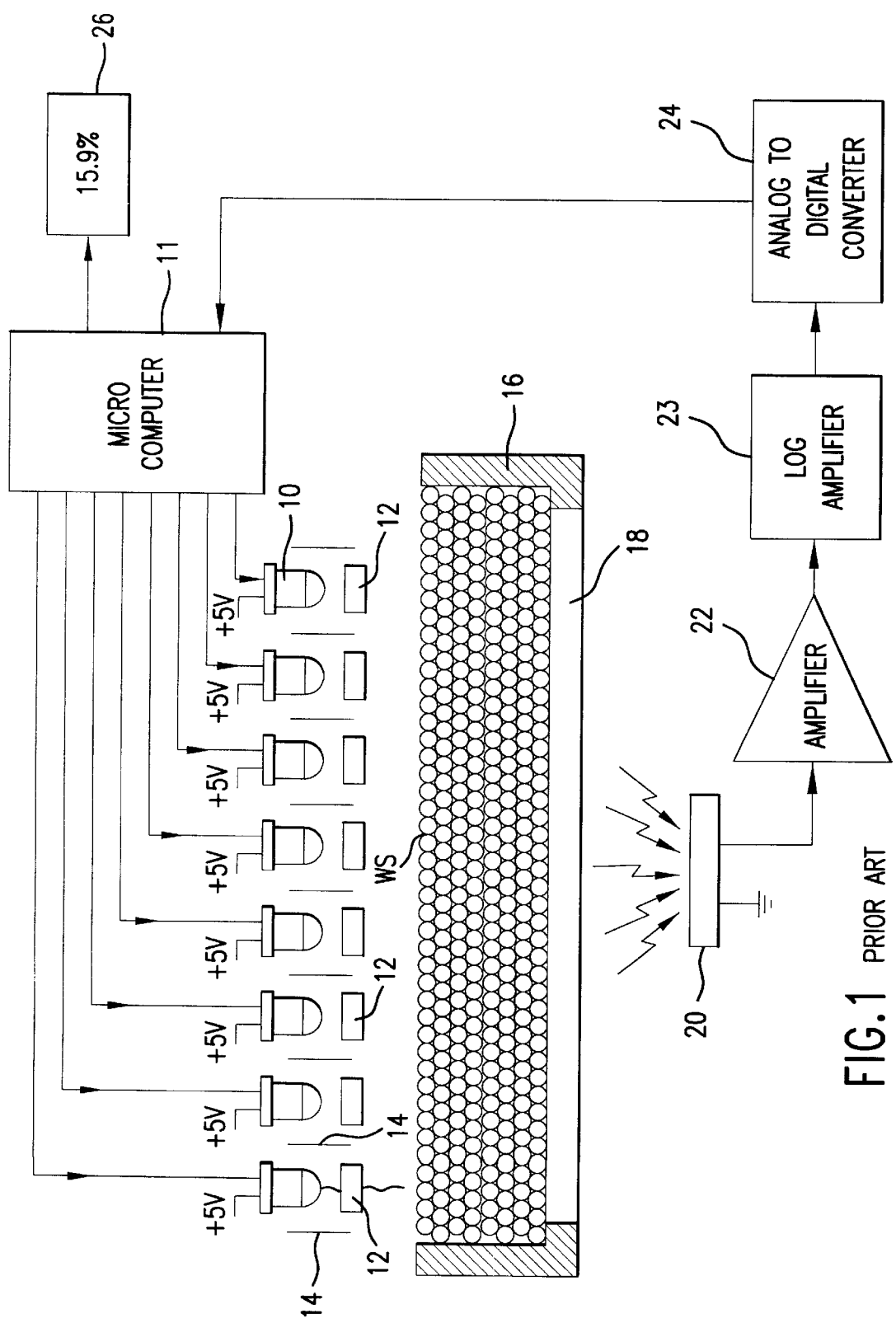
FIGS. 1–2 (Prior Art) are schematic diagrams of known Near Infrared measurement devices.
Figure 2:
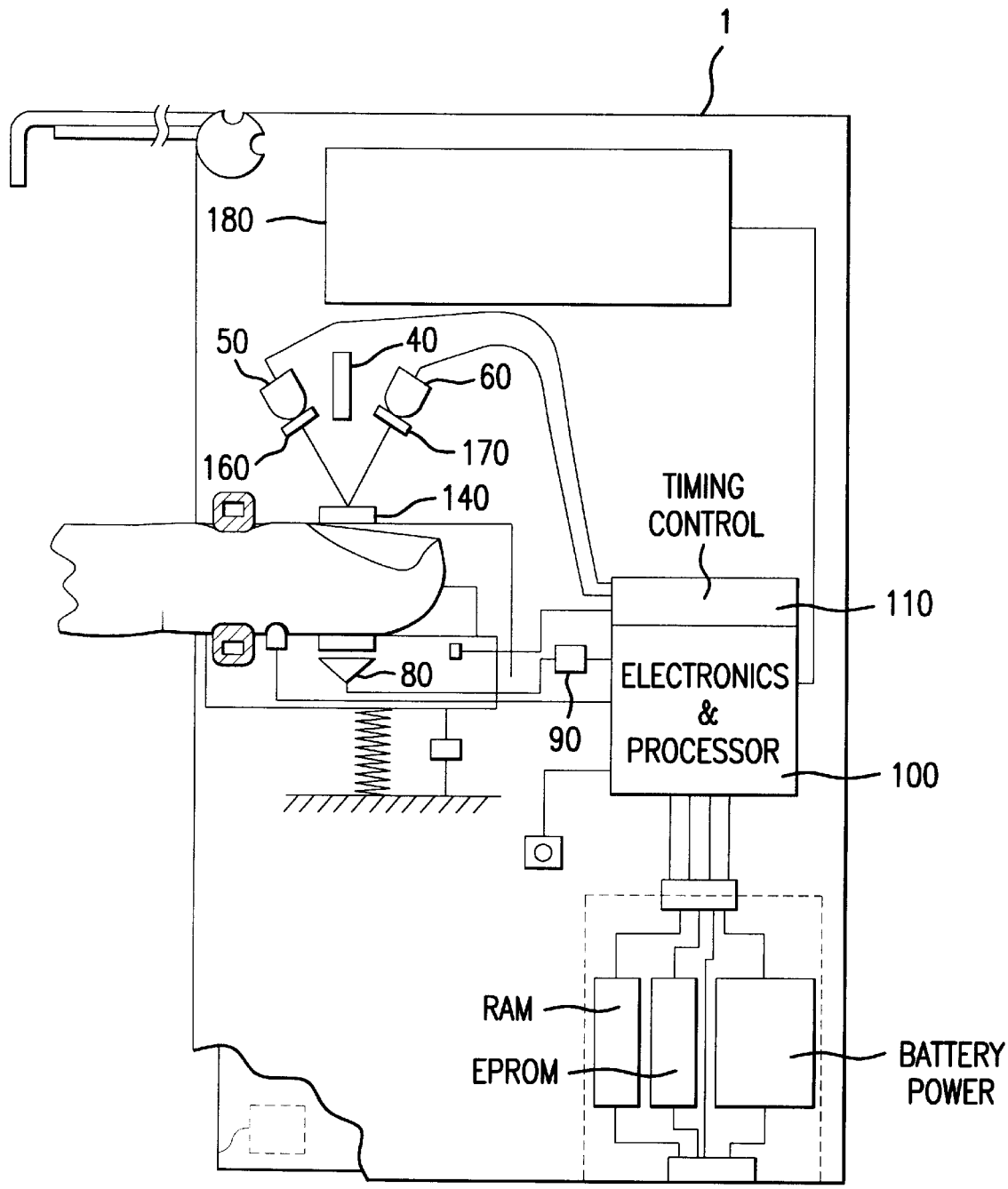
Figure 3:
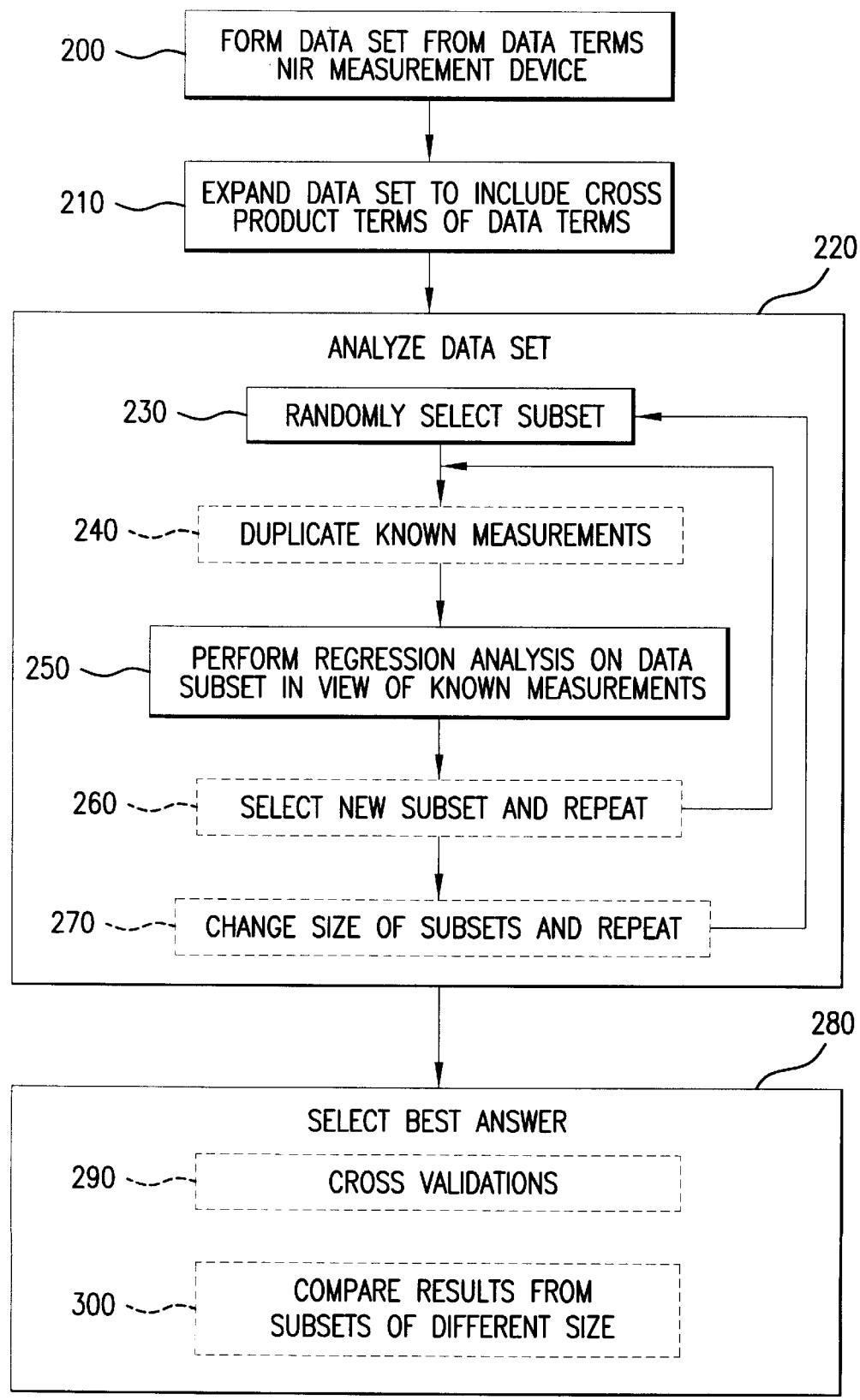
FIG. 3 is a flow diagram detailing a method in accordance with an embodiment of the present invention.

FIG. 3 illustrates a method for improving the calibration of a near infrared ("NIR") measurement device. In this method, a plurality of data terms is formed for the NIR measurement device, step 200, using known means. Then, terms representing the codependence of the data terms are formed, step 210, generally in the form of a cross-product. A cross-product, also called the covariance, is a measure of the codependence of data variables.

In the past, NIR analysis of nonlinear data may have included the basic optical measurements and even some of the optical measurements being raised to a power. However, no one examined the relationships of the various optical measurements. These relationships may provide much useful information. For instance, absorption of either a first wavelength or a second wavelength may provide little information on the quantity of a substance, while the simultaneous absorption of both wavelengths may be a strong measurement tool. However, no one has used the cross-product terms of the optical measurements by an NIR device. The reason for this avoidance of the cross-product terms is probably a holdover from Beer's Law that provides, as described above, that the variables are linear and separable. Also, most mathematical textbooks focus on teaching partial differentiation in cases where the variables can be separated to avoid difficult computations. In fact, difficult and tedious computations are generally required to solve inseparable differential equations.

As previously provided, the cross-product terms represent the interaction between two more variables. By using the cross-products, it is assumed that the variables are not separable and cannot be individually defined. An example of clearly nonseparable variables can be seen in light transmission through a finger. The amount of water in the finger not only affects light absorption but also light scattering in conjunction with other factors. Thus, light energy absorption and light energy scattering are dependent information that cannot be separated.

The basic idea for cross-products is well known and can be described using a power series expansion to describe the relationship of two variables, X and Y:

a zero order polynomial expansion is a constant;

a first order polynomial expansion has a constant, Y and X; and a second order polynomial expansion may have the following terms: a constant, X, Y, $X^2$, $Y^2$, and $X \otimes Y$, where $X \otimes Y$ represents the cross-product of X and Y.

Performing NIR measurements using linear approximations based on Beer's Law, i.e., fitting the data to a straight line, is equivalent to using the first order polynomial expansion.

In a typical near-infrared instrument, such as the ones described in the '787 and '476 patents, a limited number of discrete optical measurements are made at different wavelengths. When discrete optical measurements are made at n different wavelengths, there will be n first order terms having the form. where i$\in\{1, \ldots, n\}$, the subscript i identifies which wavelength is being measured, and $D_i$ is Log $(I_i)^{-1}$ at the wavelength corresponding to i, as previously described in equation 1.

In one known NIR measurement device, individual discrete measurements are made at 14 different wavelengths in the spectra of interest. The measurement produces fourteen discrete optical terms in the very near infrared spectra, and the first order terms would be $D_1, D_2, \ldots, D_{14}$.

If second order terms are used, including the cross-products, the second order terms would be $$D_i \otimes D_j, \quad \text{(Equation 3)}$$

where $i, j \in \{1, \ldots, n\}$, $i \leq j$, and the subscripts i and j identify wavelengths that are being measured. Thus, in the above-described NIR measurement device that makes individual discrete measurements at 14 different wavelengths in the spectra of interest, the cross-products from the second order are $D_1 \otimes D_1, \ldots, D_1 \otimes D_{14}, D_2 \otimes D_2, \ldots, D_{14} \otimes D_{14}$. There will be $$\tfrac{1}{2} \times n \times (n+1) \quad \text{(Equation 4)}$$

second order terms. For instance, with fourteen first order terms there are 105 distinct second order terms.

Similarly, if third order terms are considered, they would be of the form $$D_i \otimes D_j \otimes D_k, \quad \text{(Equation 5)}$$

where $i, j$ and $k \in \{1, \ldots, n\}$, $i \leq j \leq k$, and the subscripts i, j and k identify which of the n wavelengths are being measured. For example, in an NIR measurement device that makes individual discrete measurements at fourteen different wavelengths in the spectra of interest, the third order terms are $D_1 \otimes D_1 \otimes D_1, \ldots, D_1 \otimes D_1 \otimes D_{14}, \ldots, D_{14} \otimes D_{14} \otimes D_{14}$. There will be $$\tfrac{1}{2} \times \tfrac{1}{3} \times n \times (n+1) \times (n+2) \quad \text{(Equation 6)}$$

unique third order terms. Thus, with fourteen first order terms, there are 560 distinct third order terms.

In a preferred embodiment of the present invention, both first, second, and third order terms are considered during the statistical analysis. As can be seen from Equations 5 and 6, the number of possible terms rapidly increases when considering second and third order terms. For instance, the NIR measurement device that makes individual discrete measurements at 14 different wavelengths produces a total of 679 first, second and third order terms. This large number of potential terms makes it difficult to use the cross-products terms to calibrate the NIR measurement device. Present statistical techniques and limits on the number of sample data do not allow for the fast and simple statistical analysis of large number of data terms.

As seen in FIG. 3, the next step of the method of the present invention, step 220, is to perform statistical analysis on the data terms and the cross-product terms. However, as described above, there tends to be a large total number of data and cross-product terms.

In statistics, it is well known to approximate the results of a large population by sampling a small representative group. For example, the outcome of an election may be reliably predicted by sampling a small group of voters. A meaningful statistical result for the total population of the United States, with a reasonable confidence of 95%, may be achieved by polling as few as 1,000 people.

The present invention applies the same concept to the potentially large set of the first, second and third order terms by randomly selecting smaller subsets of terms to obtain an optimal calibration. For convenience, this approach is entitled "Monte Carlo Regression." In this approach, a number of variable terms are randomly selected, step 230, and used in a statistical analysis such as Multiple Linear Regression ("MLR"), step 250. Many statistical techniques to analyze data are known and may be used. For instance, it is known to use Nonlinear Regression Analysis ("NRA") for curve fitting to find a nonlinear equation that best fits a set of data values. In using NRA, the final solution may be in the form of polynomial, exponential, logistic, periodic, or general nonlinear functions.

The random selection and analysis of the steps 230 and 250 continue until a desired solution is produced, or a certain number of iterations are achieved, step 260. Then random selection and analysis of the steps 230 and 250 may be repeated with a different number of data terms, step 270.

To implement the Monte Carlo Regression, a computer program is written to include all the available potential regression terms. In the case of fourteen first order terms, the computer program may access all 679 possible first, second, and third order terms. The program further includes data that contains the results of readings of samples made with the NIR device as well as accurate measurements of the same samples taken from other known methods, such as laboratory testing.

One issue that arises is how to select from the multitude of possible measurement terms be included in the NIR calibration analysis. For example, in a typical NIR calibration there may be 150 optical measurement samples, e.g., 150 different measurements from the NIR device to be compared to the results of laboratory measurements. With 150 samples, up to twenty potential variable terms could be included in the calibration analysis because robust calibration design requires at least seven samples per variable term. Thus, the question is how to select the best subset of terms from the large set of first, second third order terms.

The computer program accepts an inputted number A or a range of numbers $A_1$ through A2 that represents the number or numbers of desired variable regression terms to be analyzed at a time by the computer. For example, the number of variables could be limited to 15, 25 or any other integer. With fourteen first order terms, the computer may typically search for the best selection of twelve through twenty-two variable terms. It should be understood however, that any number A of terms may be used.

In performing statistical analysis, it is recognized that the more variable terms that are included, the better the statistical result would appear to be. However, such better results may cause poorer forward prediction capability because they may be overfitting the data.

Normally, it would be preferred to have an independent set of samples that could be used in a prediction mode to test the robustness of the calibration. Unfortunately, this is simply not possible with the NIR measurement of many materials, such as blood glucose.

Historically, this type of problem was resolved by limiting the total number of variables so that the number of samples per variable was above some threshold. For example, it is typical to use ten samples per variable as the minimum amount used. When using 10 samples per variable, at least 150 samples are required to analyze fifteen variables. In the technical literature, it is generally recommended that at least five or six samples per variable term be used.

The following table provides the limit on the number of variables, i.e., the number of regression terms, that could be used from 150 samples. As seen in the table, the number of variables depends on the number of samples per variable.

TABLE 1

| Number of Samples Per Variable | Number of Variables from 150 Sample Calibrations |
| --- | --- |
| 4 | 38 |
| 5 | 30 |
| 6 | 25 |
| 7 | 21 |
| 8 | 19 |
| 9 | 17 |
| 10 | 15 |

Generally, the calibration is limited to at least seven samples per variable or a maximum of 20 calibration terms from 150 samples.

The computer program may also accept a second input B that represents the number of iterations or regression attempts to be performed (such as one million) for each number of variable terms being analyzed. With greater B values, the program produces more accurate results but runs for longer time periods because of the increased number of computations.

The program then randomly selects and saves A terms from the data set of multiple possible terms and performs the statistical analysis. The program then randomly selects another set of A terms and repeats the analysis. The program replaces the first set with the second set if the statistical analysis shows the second set to be better, i.e., to have higher correlation coefficient than the first set of terms. The program continues this process of random selection and regression analysis until it has completed all B iterations. At this point, the program provides the calibration constants and the statistics for the best combination of A terms it found in the B attempts.

Obviously, there may be better combinations that were not randomly selected by the program after B iterations. However, studies have shown that any improvement by additional iterations (for example, using 100 million iterations instead of one million) is quite small.

Then in step 280, this best solution is selected. In using the Monte Carlo program with a large number of variable terms, such as twenty, it is possible to derive extremely large calibration constant value K, sometimes more than 300,000. The reason for this result is that the statistical analysis of step 250 derives the best possible fit. Sometimes that fit results in overfitting, which contorts the calibration by deriving very large calibration constants.

The Monte Carlo program may provide, along with a best answer, some different answers that are almost as good. Normally, some of these next best answers have calibration constants that are more reasonable but result in minor degradation of the calibration statistics. Thus, an alternative set of calibration terms may be selected based upon the following criteria:

1) The Figure of Merit ("FM") of the calibration would not be diminished more than 0.2, where FM is defined as the range of laboratory data, i.e., the highest lab value minus the lowest lab value, divided by two times the standard error of deviation, and
2) The calibration constants are significantly reduced compared to the best solution. Accordingly, in a preferred embodiment of the present invention, the step of selecting the best solution, step 280, is achieved by selecting a solution with a high FM value and a reasonable calibration constant.

In addition, once the program finds the best solution for the A numbered wavelength terms, the program may optionally perform a cross validation study on this best result, step 290, as part of selecting the best solution. During the cross validation study, the set of the A best terms produced during the above process are further analyzed as follows:

(1) The program first leave out the first sample and uses the wavelength terms to do a linear regression of the remaining A-1 samples to derive a new set of calibration constants. The program then multiplies these new calibration constants with the optical data of the first sample to obtain and store a predicted value for the first sample.

(2) The program then returns the removed sample to the data set, removes a second sample and repeats the regression analysis with the remaining A-1 samples. Then, the program would again use the results of the regression analysis to form and store a prediction of the removed second sample.

(3) The program continues this process of removing and predicting samples until all samples in the best solution set have been predicted using the remaining members of the set. The program then take compares the predicted sample values to the actual sample values to give an overall indication of the quality of the calibration.

However, as suggested above, the best calibration result may not provide the best prediction result for calibration. Accordingly, the program allows a user to input a variable N that directs the program to save the N solutions that have the closest correlation to the single best solution. In a typical case, the program saves ten solutions and performs cross validation on all ten. The program then selects the solution that produces the best cross validation result.

When the user specifies a range of numbers, $A_1$ through $A_2$, the same procedure will be then repeated for subsets with $A_1+1$ variables, then subsets with $A_1+2$ variables, and so on until the program reaches the $A_2$ limit. Thus, a best solution may be selected for each of the selected sizes for the data term subset. Then, the program compares the best solution for each of the sizes of the data term subsets to find an overall best solution, step 300. The overall best solution is the subset that provides the solution having highest cross validation correlation.

The approach of the present invention may be further adapted to included other types of measurement data as part of the step of creating the data terms, step 200, because other physical parameters may provide additional information concerning blood glucose level. To use these other measurements, the program is amended to include additional data terms for consideration during the Monte Carlo Regression. These other parameters include the test subject's pulse rate and the logarithmic value of the pulse rate. The pulse rate may be easily measured by the NIR measurement device when taking the blood glucose levels. Another pair of possible parameters are the test subject's finger temperature and the logarithmic value of the finger temperature, as described in U.S. Pat. No. 4,466,076 issued on Aug. 14, 1984 to Rosenthal, the entire subject matter of which is also incorporated by reference. The method of present invention may further consider the time period from previous meals. For instance, the program may consider various "meal data" terms, such as the six variables described in U.S. Ser. No. 09/073,941 filed on May 6, 1998 by Rosenthal, the entire subject matter of which is hereby incorporated by reference.

In addition to these ten terms, the IRED temperature and the NIR detector temperature, along with the logarithmic values of the IRED temperature and the detector temperature, may improve the calibration of the NIR measurement device. However, the use of these temperature terms may be risky because they may provide a false data correlation during data analysis. For this reason; these four temperature terms are generally not used.

The calibration may be further improved by using the NIR measurement data from more than one finger. More specifically, if a single finger is used in the calibration, then the forward prediction capability of the instrument diminishes, and in fact, disappears after a short period of time, such as in weeks. The reason for this loss in prediction ability is believed to be due to changes in the chemical composition of the finger. As previously discussed, a typical finger has approximately 55% to 80% water, 5% to 35% fat and 4% to 12% muscle. Over an extended period of time, a finger's water-to-fat ratio will change. It is believed that this change is one reason that single finger calibrations do not have the robustness in predicting blood glucose.

The use of three different fingers in the calibration provides a more robust calibration. Typically, NIR measurements are taken from the index, the middle or the ring fingers. The spectral data generally shows large differences in the water-to-moisture ratios for these three fingers. For example, the ring finger has the most fat, and the index finger has the least amount of fat. Thus, taking a measurement of three fingers during each a laboratory reading, the calibration is able to account for a large change in internal chemistry of a single finger that may occur over time, as well as changes in the size of the finger that may occur in the future.

While the use of three fingers will diminish the apparent accuracy of the calibration of the unit, the practice produces a more robust calibration that allows better long-term predictions.

Another benefit of this three-finger calibration approach is that it significantly reduces the number of finger sticks, i.e., laboratory measurements, required during the calibration process. For example, if the calibration program requires 150 samples, this number of samples could be generated using only fifty finger stick readings. Reducing the number of finger stick readings produces a considerable savings in cost and time while performing the calibration. For example, if a typical person tests one finger four times a day during the calibration procedure, it would require 38 days to generate 150 calibration samples. If the person tests three fingers four times per day, it would only require thirteen days to generate the same number of samples.

As described above, the accuracy of the calibration is decreased by using measurements from three fingers. This loss of accuracy can be minimized by the following procedure that skews the calibration in favor of the finger to be measured:

1) Decide what finger is to be used for future measurements (usually the left index finger);
2) Duplicate all data for that finger three times; and
3) Add these duplicates to the set of reliable readings.

With the above approach, approximately two-thirds of the total samples in the calibration file will be of the selected finger. The other third will be equally split between the other two fingers.

In another embodiment, NIR readings are taken from three fingers from both of a user's hands. Then the above described procedure is repeated for each hand.

This approach can be logically explained by considering all the calibration samples to have a normal, i.e., bell shape, distribution. The test of selected finger being duplicated three times can be considered fitting within the one standard deviation limit, which is approximately 68% of all samples. The other two fingers which numerically correspond to approximately 33% of the total can be considered as the samples outside the standard deviation.

The example below illustrates the improvements in calibration accuracy from the use of second order and third order optical terms. This improvement in the calibration accuracy is generally significant. For instance, the use of second and third order terms typically almost doubles the coefficient of determination.

EXAMPLE 1

Figure 4:
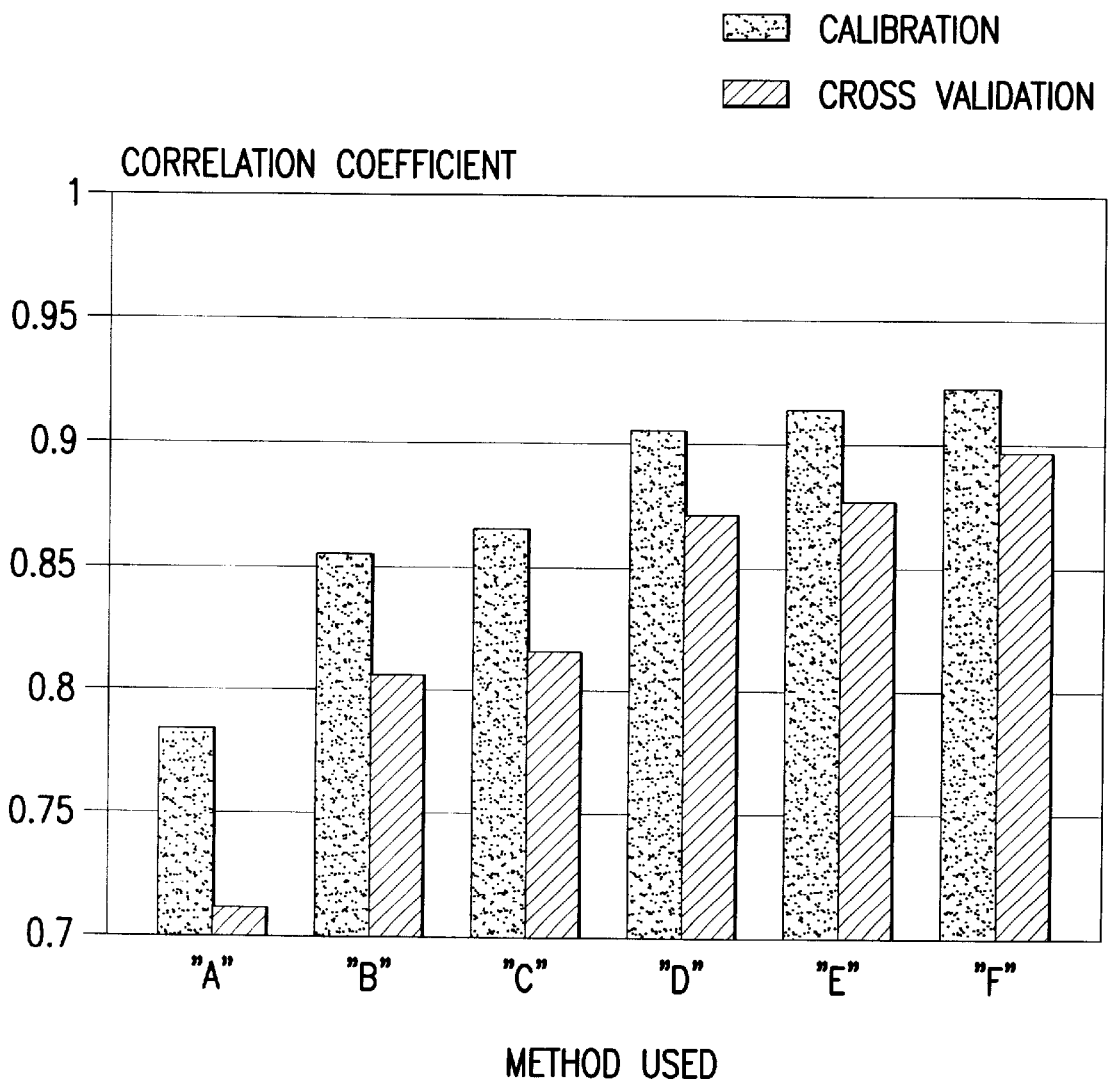
FIGS. 4–6 are charts illustrating experimental results of implementing the present invention.

FIG. 4 illustrates a calibration performed on a diabetic individual for blood glucose measurement with an NIR device that uses the fourteen wavelengths. Using first order terms from the fourteen basic wavelengths provided a cross validation correlation of 0.710, bar A in FIG. 4. As illustrated in the next bar, B, using the combination of first and second order terms provided a cross validation correlation of 0.806. The next bar to the right, C illustrates the result of using the combination of first, second and third order terms and provides an improved result of 0.816. The use of nonoptical data terms, along with the combination of first, second and third order optical terms, improved cross validation correlation to 0.898, column F.

Figure 5:
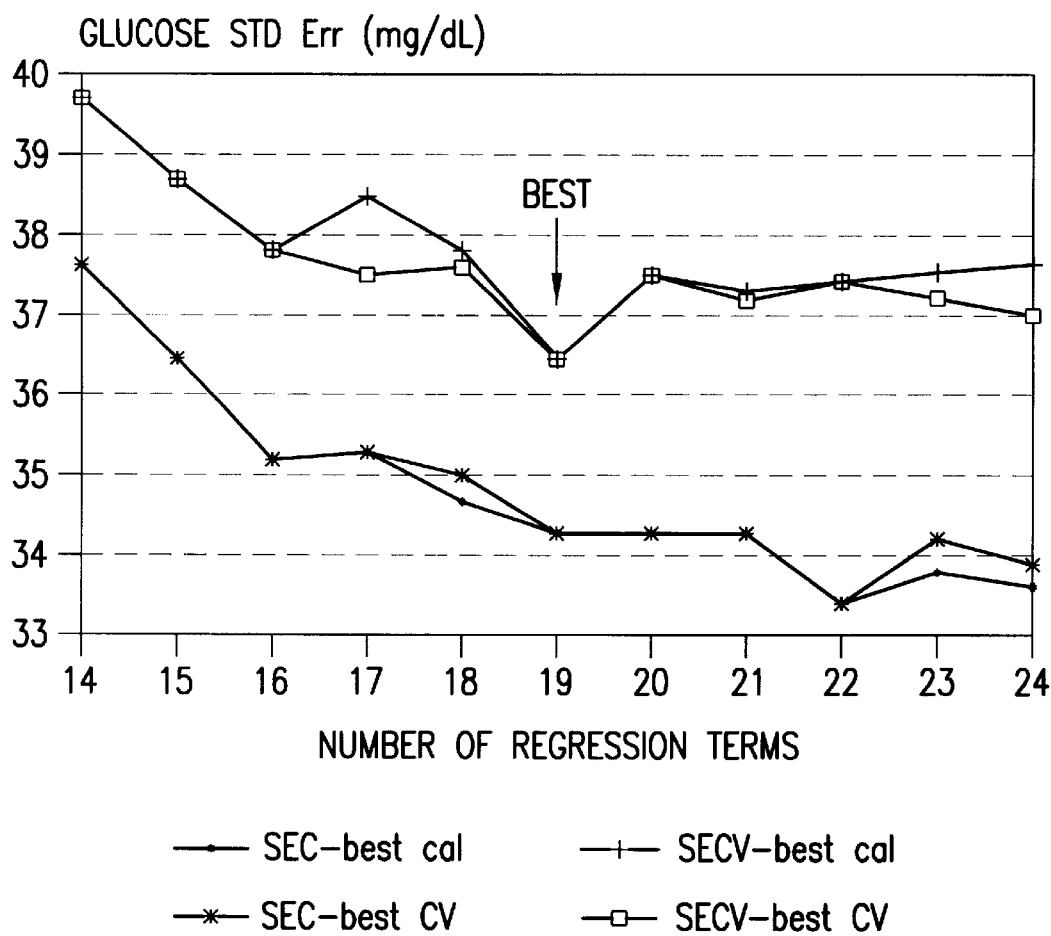

FIG. 5 illustrates the effect of adjusting the number of variable terms used, as shown by the standard error of the calibration and the standard error of cross validation. The key parameter is the standard error of cross validation because it is a measure of the predictability of the calibration. In this instance, the best result was achieved using nineteen terms that included a combination of first, second and third order optical terms as well as some physical terms. Thus, using the larger numbers of terms may not improve the calibration.

Figure 6:
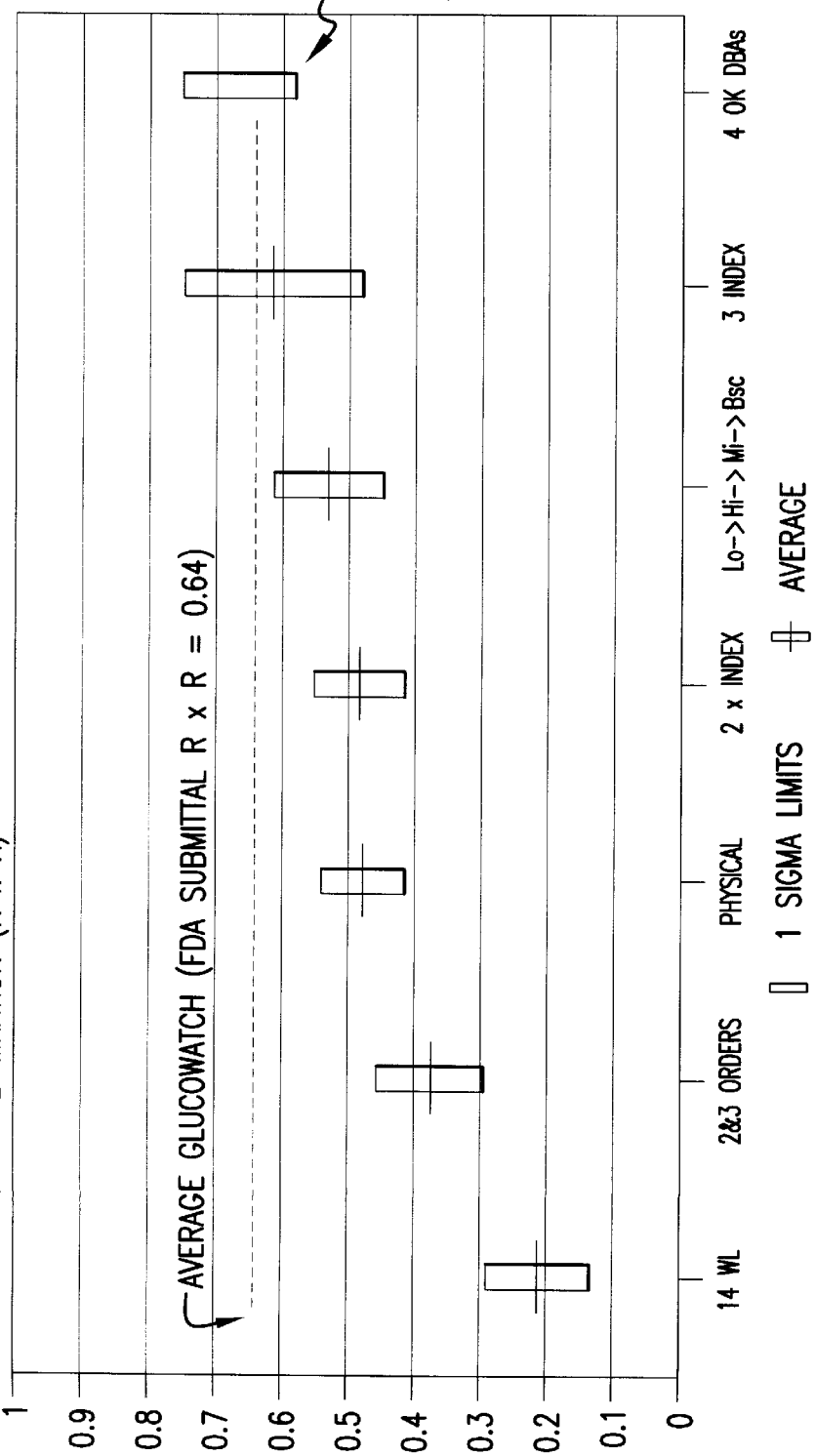

The benefits of the method of the present invention are further illustrated in FIG. 6 that summarizes the average of six randomly chosen NIR measurement devices from a fourteen-day home calibration study. The most left "bar" in FIG. 6 is the Coefficient Of Determination (the correlation coefficient squared) when using only the First Order terms. The next bar to the right shows that the Coefficient Of Determination is much greater when the first, second and third order terms are used. The third bar from the left in FIG. 6 demonstrates the improvement to Coefficient of Determination by combining the "physical terms" with the optical terms. All results presented in FIG. 6 were produced with the Monte Carlo approach using twenty variables, except for the leftmost bar that used only the fourteen first order terms. In addition, all data in this example were derived using the weighted three finger approach.

The above-results, illustrated in FIGS. 4–6, were obtained using a relatively lowcost personal computer, having a 400 MHz Celeron® Processor produced by the Intel Corporation of Santa Clara, Calif. The computer was able to complete one million interactions in approximately one hour. Thus, the approach described herein is practical, economical and easily achievable.

As part of the step of analyzing the ability of the data terms subsets to predict the results of reliable measurements, step 250, the method of the present invention may be optionally adapted to skew the reliable measurements to produce nonoptimal calibrations that provide better results over a desired data range, step 240. The need for this step is now discussed.

One characteristic of using statistical analysis is that the accuracy of predicted samples at the low end and high end of the calibration range may not be as good as the accuracy in the middle of the calibration range. Moreover, if the calibration range is very large, as is true in the NIR blood glucose measurement system, then the predicted values of low glucose samples tend to be much higher than the actual value, causing an unacceptable risk of hypoglycemia. Similarly, the predicted values of high glucose samples tend to be much lower than actual values, limiting the usefulness of the NIR measurement device in hyperglycemic control. Moreover, the predicted values of samples in the middle part of the glucose range may also have large glucose errors, over or under the actual values, because the statistical analysis attempts to fix a line between the high and low glucose samples.

Research using an NIR device to predict octane numbers in gasoline has shown that increasing the number of samples at the low end of the range of possible values provides a calibration that improves prediction values at the low end of the range of values. The number of samples at the low end of the range of values may be increased by simply repeating the same samples that exist at the low end some number of times. For instance, the same low-end values may be used ten times. However, this new low calibration will have less accuracy over the entire range, especially at the high end of the range of possible values.

Similarly, increasing the number of samples at the high end of the possible range of values achieves a much better calibration for predicting high value. Again, the number of samples may be increased by simply reusing or repeating the samples having high levels of the measured material. The high end calibration will have less accuracy over the entire range, especially at the low end of the range of possible values.

Unfortunately, there is no known method of determining the number of duplicates to choose, and what limits to establish for the low end and for the high end.

In response to this problem, a multistep, parametric approach may be used to improve the calibration. This approach is discussed with reference to blood glucose testing, but is not limited to that application. The multistep approach is equally applicable to any NIR measurements. For instance, in blood glucose measurements, the "Low Region" is defined as glucose values less than 120 mg/dL. This Low Region is further subdivided into three subsections: Low Region 1 that ranges from 100 to 120 mg/dL; Low Region 2 that ranges from 99 to 70 mg/dL; and Low Region 3 that includes values below 70 mg/dL. The three Low regions are evaluated in three steps. In the first evaluation step, the new set calibration data is created to include all samples plus a duplicate of the samples in Low Region 1, two duplicates of the samples in Low Region 2, and three duplicates of the samples in Low Region 3. In the second step, a second new calibration data file is created that includes all samples plus a single duplicate of the samples in Low Region 1, three duplicates of the samples in Low Region 2, and five duplicates of the samples in Low Region 3. In the third step, a third new calibration data file is created that includes all samples plus two duplicates of the samples in Low Region 1, five duplicates of the samples in Low Region 2, and ten duplicates of the samples in Low Region 3. The procedure thus provides three separate Low calibration files to be evaluated using the general Monte Carlo approach.

For the purpose of blood glucose measurements, the "High Region" is defined as containing all samples that have glucose values greater than 240 mg/dL. This High Region is further subdivided into three Sections: High Region 1 with blood glucose levels between 240 and 295 mg/dL; High Region 2 with blood glucose levels between 296 and 350 mg/dL; and High Region 3 with blood glucose levels between 351 and 400 mg/dL. The High Regions are evaluated in three alternate steps. In the first step, a new calibration data file is created that includes all samples plus a duplicate of the samples in region High 1, two duplicates of the samples in region High 2, and three duplicates of the samples in region High 3. In the second step, a second new calibration data file is created that includes all samples plus a single duplicate of the samples in region High 1, three duplicates of the samples in region High 2, and five duplicates of the samples in region High 3. In the third step, a third new calibration data file is created that includes all samples plus two duplicates of the samples in region High 1, five duplicates of the samples in region High 2, and ten duplicates of the samples in region High 3. The above procedure provides three separate High calibration files to be evaluated using the Monte Carlo approach.

In blood glucose tests, the "Mid Region" is defined as all samples that were between 121 and 239 mg/dL. This Mid Region may also be evaluated by generating three alternate calibration files. One new calibration data file includes all calibration samples plus one duplicate of the samples in the Mid Region. In a second calibration file, the samples in the Mid Region are duplicated three times. In a third calibration file, the samples in the Mid Region are duplicated five times.

The Monte Carlo Program then provides the statistical analysis results for ten different calibration files: the original data file, the three "Low Region" files, the three "High Region" files, and three "Mid Region" files. An appropriate calibration result may then be selected according to the needs of the user.

The use of the alternative calibration is now described in greater detail. FM values are determined for the terms of the data term set. If the FM value is acceptable, such as 2.5 or greater, Monte Carlo analysis is performed on all nine Low, Mid and High Regions data files, defined above, as well as the original calibration. More specifically, a preferred embodiment uses the following criteria:

(A) if FM<2.5, the calibration is unreliable and should not be used;

(B) if 2.5<FM<2.9, the calibration is usable but with caution;

(C) if 3.0<FM<4.9, there is a good calibration; and (D) if FM<5.0, the calibration is excellent.

Each of the ten different data sets is then used to determine a separate set of optimum wavelengths terms and their associated calibration constants. With an NIR device with fourteen first order wavelength terms and original 150 NIR measurement samples, it is typical to seek approximately twenty optimum wavelengths terms for each of the ten calibrations, as described above.

Using the ten different calibrations allows the NIR measurement device to derive more accurate glucose values over the large range of possible values. For simplicity, the following discussion assumes that there is only one Low calibration, only one High calibration and only one Mid calibration. However, it should be appreciated that multiple Low, Mid, and High calibrations may be performed, and optimally, nine Low, Mid, and High calibrations are performed.

First, the glucose level of the sample is predicted using the Low Range calibration's wavelengths and constants. If the predicted result is below 120 mg/dL, the NIR measurement device is calibrated using the Low Range calibration's wavelengths and constants.

If the predicted result using the Low Range calibration is above 120 mg/dL, the glucose level of the sample is first predicted using the High Range calibration. If the predicted result from High Range calibration is greater than 240 mg/dL, the NIR measurement device is calibrated using the High Range calibration's wavelengths and constants.

If neither the Low Range nor the High Range calibrations are used, the measurement then is predicted from the sample data using the MID Range calibration. If the predicted result with the Mid Range calibration is between 120 and 240 mg/dL, the NIR measurement device uses the Mid Range's calibration wavelengths and constants.

Otherwise, the NIR measurement device is calibrated using the basic calibration without any duplication of sample data in any of the ranges.

The NIR blood glucose determinations from using the selected calibration are then placed into a data file, including the number of samples and their laboratory values. Using this data file, the calibration statistics are determined for comparison to using various criteria, such as above-described protocol for the FM values to determine if the calibration is acceptable.

In one embodiment, there are 27 combinations of the three Low Range, the three High Range, and the three Mid Range calibrations to be evaluated. The following table illustrates the results of a calibration using this embodiment of the calibration method. The experiment used the various alternative calibrations to find the calibration with the highest correlation and FM value (shown in bold).

TABLE 2

Low/High Thresholds

Low = 120
High = 240

| | Filename | # Samples | LoGlucose | HiGlucose |
|---|---|---|---|---|
| Input Data File: | 40020G.ALL | 312 | 55 | 372 |
| High 1 | 40020020.001 | 474 | 20 | 400 |
| High 2 | 40020120.001 | 486 | 20 | 400 |
| High 3 | 40020220.001 | 624 | 20 | 400 |
| Low 1 | 40020320.001 | 444 | 20 | 400 |
| Low 2 | 40020420.001 | 456 | 20 | 400 |
| Low 3 | 40020520.001 | 576 | 20 | 400 |
| Middle 1 | 40020620.001 | 474 | 20 | 400 |
| Middle 2 | 40020720.001 | 798 | 20 | 400 |
| Middle 3 | 40020820.001 | 1122 | 20 | 400 |
| Unweighted | 40020920.001 | 312 | 20 | 400 |

---------- Calibration Results - Middle 1 ----------

| | 1-Touch Average | High 1 Low 1 | High 1 Low 2 | High 1 Low 3 | High 2 Low 1 | High 2 Low 2 | High 2 Low 3 | High 3 Low 1 | High 3 Low 2 | High 3 Low 3 |
|---|---|---|---|---|---|---|---|---|---|---|
| *ALL FINGERS* | | | | | | | | | | |
| Average | 184.3 | 188.7 | 187.3 | 186.4 | 190.3 | 189.0 | 188.0 | 192.8 | 191.4 | 190.5 |
| Std Dev | 76.8 | 67.2 | 68.4 | 69.5 | 68.9 | 70.1 | 71.3 | 71.6 | 72.8 | 73.9 |
| - Basic Stats - | | | | | | | | | | |
| Correlation | | 0.726 | 0.740 | 0.735 | 0.750 | 0.762 | 0.758 | 0.748 | 0.760 | 0.756 |
| Std Err Pred | | 54.146 | 53.011 | 53.665 | 52.415 | 51.242 | 51.918 | 53.594 | 52.448 | 53.108 |
| Figure Merit | | 2.932 | 2.995 | 2.958 | 3.029 | 3.098 | 3.058 | 2.962 | 3.027 | 2.989 |
| - With Bias Correction - | | | | | | | | | | |
| Bias | | -4.3 | -3.0 | -2.0 | -6.0 | -4.6 | -3.7 | -8.5 | -7.1 | -6.2 |
| Average | | 184.3 | 184.3 | 184.3 | 184.3 | 184.3 | 184.3 | 184.3 | 184.3 | 184.3 |
| Std Dev | | 67.2 | 68.4 | 69.5 | 68.9 | 70.1 | 71.3 | 71.6 | 72.8 | 73.9 |
| Correlation | | 0.726 | 0.740 | 0.735 | 0.750 | 0.762 | 0.758 | 0.748 | 0.760 | 0.756 |
| Std Err Pred | | 53.971 | 52.928 | 53.625 | 52.066 | 51.030 | 51.783 | 52.916 | 51.963 | 52.745 |
| Figure Merit | | 2.941 | 2.999 | 2.960 | 3.049 | 3.111 | 3.066 | 3.000 | 3.055 | 3.010 |
| - With Slope/Bias Correction - | | | | | | | | | | |
| Slope | | 0.830 | 0.831 | 0.812 | 0.835 | 0.834 | 0.816 | 0.802 | 0.801 | 0.784 |
| Average | | 184.3 | 184.3 | 184.3 | 184.3 | 184.3 | 184.3 | 84.3 | 184.3 | 84.3 |
| Std Dev | | 55.8 | 56.8 | 56.5 | 57.5 | 58.5 | 58.2 | 57.4 | 58.3 | 58.0 |
| Correlation | | 0.726 | 0.740 | 0.735 | 0.750 | 0.762 | 0.758 | 0.748 | 0.760 | 0.756 |
| Std Err Pred | | 52.751 | 51.644 | 52.005 | 50.803 | 49.687 | 50.089 | 50.973 | 49.904 | 50.275 |
| Figure Merit | | 3.009 | 3.074 | 3.053 | 3.125 | 3.195 | 3.169 | 3.114 | 3.181 | 3.158 |
| *INDEX FINGER ONLY* | | | | | | | | | | |
| Average | 184.3 | 188.2 | 186.1 | 185.6 | 190.2 | 188.2 | 187.6 | 192.2 | 190.2 | 189.6 |
| Std Dev | 77.0 | 64.0 | 66.2 | 67.2 | 65.8 | 68.1 | 69.0 | 67.6 | 69.9 | 70.8 |
| - Basic Stats - | | | | | | | | | | |
| Correlation | | 0.841 | 0.851 | 0.847 | 0.872 | 0.881 | 0.876 | 0.867 | 0.876 | 0.872 |
| Std Err Pred | | 41.811 | 40.447 | 41.031 | 38.130 | 36.630 | 37.273 | 39.131 | 37.670 | 38.296 |
| Figure Merit | | 3.797 | 3.925 | 3.869 | 4.163 | 4.334 | 4.259 | 4.057 | 4.214 | 4.145 |

TABLE 2-continued

- With Bias Correction -

| | | | | | | | | | |
|---|---|---|---|---|---|---|---|---|---|
| Bias | | -3.9 | -1.8 | -1.3 | -5.9 | -3.8 | -3.3 | -7.9 | -5.9 | -5.3 |
| Average | | 184.3 | 184.3 | 184.3 | 184.3 | 184.3 | 184.3 | 184.3 | 184.3 | 184.3 |
| Std Dev | | 64.0 | 66.2 | 67.2 | 65.8 | 68.1 | 69.0 | 67.6 | 69.9 | 70.8 |
| Correlation | | 0.841 | 0.851 | 0.847 | 0.872 | 0.981 | 0.876 | 0.867 | 0.876 | 0.872 |
| Std Err Pred | | 41.630 | 40.405 | 41.012 | 37.671 | 36.426 | 37.129 | 38.321 | 37.208 | 37.929 |
| Figure Merit | | 3.813 | 3.929 | 3.871 | 4.214 | 4.358 | 4.276 | 4.143 | 4.267 | 4.185 |

- With Slope/Bias Correction -

| | | | | | | | | | |
|---|---|---|---|---|---|---|---|---|---|
| Slope | | 1.013 | 0.990 | 0.971 | 1.020 | 0.996 | 0.977 | 0.988 | 0.966 | 0.948 |
| Average | | 184.3 | 184.3 | 184.3 | 184.3 | 184.3 | 184.3 | 184.3 | 184.3 | 184.3 |
| Std Dev. | | 64.8 | 65.6 | 65.2 | 67.2 | 67.8 | 67.5 | 66.8 | 67.5 | 67.1 |
| Correlation | | 0.841 | 0.851 | 0.847 | 0.872 | 0.881 | 0.876 | 0.867 | 0.876 | 0.872 |
| Std Err Pred | | 41.622 | 40.399 | 40.964 | 37.647 | 36.425 | 37.097 | 38.313 | 37.131 | 37.752 |
| Figure Merit | | 3.814 | 3.930 | 3.875 | 4.217 | 4.358 | 4.279 | 4.143 | 4.275 | 4.205 |

--------------- Calibration Results - Middle 2 ---------------

| | 1-Touch Average | High 1 Low 1 | High 1 Low 2 | High 1 Low 3 | High 2 Low 1 | High 2 Low 2 | High 2 Low 3 | High 3 Low 1 | High 3 Low 2 | High 3 Low 3 |
|---|---|---|---|---|---|---|---|---|---|---|

ALL FINGERS

| | | | | | | | | | | |
|---|---|---|---|---|---|---|---|---|---|---|
| Average | 184.3 | 187.9 | 186.5 | 185.5 | 189.9 | 188.6 | 187.6 | 192.6 | 191.2 | 190.2 |
| Std Dev | 76.8 | 67.0 | 68.1 | 69.4 | 68.8 | 69.9 | 71.2 | 71.5 | 72.6 | 73.8 |

- Basic Stats -

| | | | | | | | | | | |
|---|---|---|---|---|---|---|---|---|---|---|
| Correlation | | 0.733 | 0.748 | 0.744 | 0.752 | 0.766 | 0.762 | 0.750 | 0.763 | 0.759 |
| Std Err Pred | | 53.405 | 52.067 | 52.734 | 52.110 | 50.738 | 51.422 | 53.314 | 51.974 | 52.642 |
| Figure Merit | | 2.973 | 3.049 | 3.010 | 3.046 | 3.129 | 3.087 | 2.978 | 3.054 | 3.016 |

- With Bias Correction -

| | | | | | | | | | | |
|---|---|---|---|---|---|---|---|---|---|---|
| Bias | | -3.6 | -2.2 | -1.2 | -5.6 | -4.3 | -3.3 | -8.2 | -6.9 | -5.9 |
| Average | | 184.3 | 184.3 | 184.3 | 184.3 | 184.3 | 184.3 | 184.3 | 184.3 | 184.3 |
| Std Dev | | 67.0 | 68.1 | 69.4 | 68.8 | 69.9 | 71.2 | 71.5 | 72.6 | 73.8 |
| Correlation | | 0.733 | 0.748 | 0.744 | 0.752 | 0.766 | 0.762 | 0.750 | 0.763 | 0.759 |
| Std Err Pred | | 53.286 | 52.021 | 52.721 | 51.803 | 50.558 | 51.319 | 52.671 | 51.516 | 52.313 |
| Figure Merit | | 2.979 | 3.052 | 3.011 | 3.065 | 3.140 | 3.093 | 3.014 | 3.082 | 3.035 |

- With Slope/Bias Correction -

| | | | | | | | | | | |
|---|---|---|---|---|---|---|---|---|---|---|
| Slope | | 0.840 | 0.843 | 0.823 | 0.839 | 0.841 | 0.822 | 0.805 | 0.807 | 0.789 |
| Average | | 184.3 | 184.3 | 184.3 | 184.3 | 184.3 | 184.3 | 184.3 | 184.3 | 184.3 |
| Std Dev | | 56.3 | 57.4 | 57.1 | 57.7 | 58.8 | 58.5 | 57.5 | 58.6 | 58.3 |
| Correlation | | 0.733 | 0.748 | 0.744 | 0.752 | 0.766 | 0.762 | 0.750 | 0.763 | 0.759 |
| Std Err Pred | | 52.196 | 50.912 | 51.277 | 50.607 | 49.323 | 49.725 | 50.799 | 49.576 | 49.947 |
| Figure Merit | | 3.041 | 3.118 | 3.096 | 0.137 | 3.219 | 3.193 | 3.125 | 3.202 | 3.178 |

INDEX FINGER ONLY

| | | | | | | | | | | |
|---|---|---|---|---|---|---|---|---|---|---|
| Average | 184.3 | 187.1 | 184.6 | 184.0 | 189.6 | 187.1 | 186.5 | 191.8 | 189.3 | 188.7 |
| STD Dev | 77.0 | 63.6 | 66.0 | 66.9 | 65.5 | 67.9 | 68.9 | 67.3 | 69.7 | 70.6 |

- Basic Stats -

| | | | | | | | | | | |
|---|---|---|---|---|---|---|---|---|---|---|
| Correlation | | 0.838 | 0.857 | 0.853 | 0.864 | 0.881 | 0.877 | 0.859 | 0.876 | 0.871 |
| Std Err Pred | | 42.072 | 39.624 | 40.196 | 39.174 | 36.532 | 37.151 | 40.163 | 37.590 | 38.193 |
| Figure Merit | | 3.773 | 4.006 | 3.949 | 4.052 | 4.346 | 4.273 | 3.953 | 4.223 | 4.157 |

- With Bias Correction -

| | | | | | | | | | | |
|---|---|---|---|---|---|---|---|---|---|---|
| Bias | | -2.8 | -0.3 | 0.3 | -5.3 | -2.8 | -2.2 | -7.5 | -5.0 | -4.4 |
| Average | | 184.3 | 184.3 | 184.3 | 184.3 | 184.3 | 184.3 | 184.3 | 184.3 | 184.3 |
| Std Dev | | 63.6 | 66.0 | 66.9 | 65.5 | 67.9 | 68.9 | 67.3 | 69.7 | 70.6 |
| Correlation | | 0.838 | 0.857 | 0.853 | 0.864 | 0.881 | 0.877 | 0.859 | 0.876 | 0.871 |
| Std Err Pred | | 41.981 | 39.623 | 40.194 | 38.808 | 36.420 | 37.085 | 39.454 | 37.253 | 37.938 |
| Figure Merit | | 3.782 | 4.007 | 3.950 | 4.091 | 4.359 | 4.281 | 4.024 | 4.261 | 4.184 |

- With Slope/Bias Correction -

| | | | | | | | | | | |
|---|---|---|---|---|---|---|---|---|---|---|
| Slope | | 1.015 | 1.001 | 0.982 | 1.015 | 0.999 | 0.980 | 0.983 | 0.967 | 0.950 |
| Average | | 184.3 | 184.3 | 184.3 | 184.3 | 184.3 | 184.3 | 184.3 | 184.3 | 184.3 |
| Std Dev | | 64.6 | 66.0 | 65.7 | 66.5 | 67.8 | 67.5 | 66.1 | 67.4 | 67.1 |
| Correiatio | | 0.838 | 0.857 | 0.853 | 0.864 | 0.881 | 0.877 | 0.859 | 0.876 | 0.871 |
| Std Err Pred | | 41.970 | 39.623 | 40.175 | 38.795 | 36.420 | 37.059 | 39.436 | 37.184 | 37.772 |
| Figure Merit | | 3.782 | 4.007 | 3.951 | 4.092 | 4.359 | 4.284 | 4.025 | 4.269 | 4.203 |

--------------- Calibration Results - Middle 3 ---------------

| | 1-Touch Average | High 1 Low 1 | High 1 Low 2 | High 1 Low 3 | High 2 Low 1 | High 2 Low 2 | High 2 Low 3 | High 3 Low 1 | High 3 Low 2 | High 3 Low 3 |
|---|---|---|---|---|---|---|---|---|---|---|

TABLE 2-continued

ALL FINGERS

| | | | | | | | | | | |
|---|---|---|---|---|---|---|---|---|---|---|
| Average | 184.3 | 187.2 | 185.6 | 184.9 | 189.1 | 187.5 | 186.7 | 191.9 | 190.3 | 189.6 |
| Std Dev | 76.8 | 67.2 | 68.2 | 69.3 | 68.9 | 70.0 | 71.1 | 71.6 | 72.7 | 73.8 |
| - Basic Stats - | | | | | | | | | | |
| Correlation | | 0.729 | 0.752 | 0.747 | 0.749 | 0.771 | 0.766 | 0.747 | 0.768 | 0.763 |
| Std Err Pred | | 53.794 | 51.715 | 52.399 | 52.324 | 50.184 | 50.890 | 53.540 | 51.451 | 52.139 |
| Figure Merit | | 2.951 | 3.070 | 3.030 | 3.034 | 3.163 | 3.119 | 2.965 | 3.085 | 3.045 |
| - With Bias Correction - | | | | | | | | | | |
| Bias | | -2.9 | -1.3 | -0.6 | -4.8 | -3.2 | -2.4 | -7.6 | -6.0 | -5.3 |
| Average | | 184.3 | 184.3 | 184.3 | 184.3 | 184.3 | 184.3 | 184.3 | 184.3 | 184.3 |
| Std Dev | | 67.2 | 68.2 | 69.3 | 68.9 | 70.0 | 71.1 | 71.6 | 72.7 | 73.8 |
| Correlation | | 0.729 | 0.752 | 0.747 | 0.749 | 0.771 | 0.766 | 0.747 | 0.768 | 0.763 |
| Std Err Fred | | 53.714 | 51.698 | 52.396 | 52.106 | 50.085 | 50.832 | 52.997 | 51.100 | 51.873 |
| Figure Merit | | 2.955 | 3.071 | 3.030 | 3.047 | 3.170 | 3.123 | 2.995 | 3.107 | 3.060 |
| - With Slope/Bias Correction - | | | | | | | | | | |
| Slope | | 0.833 | 0.846 | 0.827 | 0.834 | 0.845 | 0.827 | 0.800 | 0.810 | 0.794 |
| Average | | 184.3 | 184.3 | 184.3 | 184.3 | 184.3 | 184.3 | 184.3 | 184.3 | 184.3 |
| Std Dev | | 56.0 | 57.7 | 57.3 | 57.5 | 59.2 | 58.8 | 57.3 | 58.9 | 58.6 |
| Correlation | | 0.729 | 0.752 | 0.747 | 0.749 | 0.771 | 0.766 | 0.747 | 0.768 | 0.763 |
| Std Err Pred | | 52.531 | 50.614 | 51.012 | 50.838 | 48.897 | 49.328 | 51.029 | 49.195 | 49.591 |
| Figure Merit | | 3.022 | 3.136 | 3.112 | 3.123 | 3.247 | 3.218 | 3.111 | 3.227 | 3.201 |
| INDEX FINGER ONLY | | | | | | | | | | |
| Average | 184.3 | 186.5 | 183.6 | 183.3 | 189.7 | 185.8 | 195.5 | 191.1 | 188.2 | 187.9 |
| Std Dev | 77.0 | 63.9 | 66.2 | 66.9 | 65.8 | 68.1 | 69.8 | 67.6 | 69.9 | 70.6 |
| - Basic Stats - | | | | | | | | | | |
| Correlation | | 0.827 | 0.858 | 0.952 | 0.853 | 0.892 | 0.876 | 0.849 | 0.877 | 0.871 |
| Std Err Pred | | 43.340 | 39.538 | 40.384 | 40.375 | 36.263 | 37.194 | 41.313 | 37.304 | 38.200 |
| Figure Merit | | 3.663 | 4.015 | 3.931 | 3.932 | 4.378 | 4.269 | 3.843 | 4.256 | 4.156 |
| - With Bias Correction - | | | | | | | | | | |
| Bias | | -2.2 | 0.7 | 1.0 | -4.4 | -1.5 | -1.2 | -6.8 | -3.9 | -3.6 |
| Average | | 184.3 | 184.3 | 184.3 | 184.3 | 184.3 | 194.3 | 184.3 | 184.3 | 184.3 |
| Std Dev | | 63.9 | 66.2 | 66.9 | 65.8 | 68.1 | 68.8 | 67.6 | 69.9 | 70.6 |
| Correlation | | 0.827 | 0.858 | 0.852 | 0.853 | 0.882 | 0.876 | 0.849 | 0.877 | 0.871 |
| Std Err Pred | | 43.285 | 39.531 | 40.371 | 40.128 | 36.230 | 37.164 | 40.747 | 37.099 | 38.031 |
| Figure Merit | | 3.668 | 4.016 | 3.932 | 3.956 | 4.382 | 4.272 | 3.896 | 4.279 | 4.174 |
| - With Slope/Bias Correction - | | | | | | | | | | |
| Slope | | 0.996 | 0.998 | 0.981 | 0.999 | 0.998 | 0.981 | 0.967 | 0.966 | 0.950 |
| Average | | 184.3 | 184.3 | 184.3 | 184.3 | 184.3 | 184.3 | 184.3 | 184.3 | 184.3 |
| Std Dev | | 63.7 | 66.1 | 65.6 | 65.7 | 67.9 | 67.5 | 65.4 | 67.5 | 67.0 |
| Correlation | | 0.827 | 0.858 | 0.852 | 0.853 | 0.882 | 0.976 | 0.849 | 0.877 | 0.871 |
| Std Err Pred | | 43.285 | 39.531 | 40.350 | 40.128 | 36.230 | 37.140 | 40.687 | 37.021 | 37.864 |
| Figure Merit | | 3.668 | 4.016 | 3.934 | 3.956 | 4.382 | 4.274 | 3.902 | 4.288 | 4.193 |

The invention, having been described, it will be apparent to those skilled in the art that the same may be varied in many ways without departing from the spirit and scope of the invention. Any and all such modifications are intended to be included within the scope of the following claims.

What is claimed is:

1. A method for calibrating a near infrared (NIR) measurement device to a subject, said method comprising the steps of:

forming a data set comprising a plurality of optical measurement data terms for said NIR measurement device;

augmenting said data set by forming cross-products terms using said data terms;

forming a plurality of subsets having a first specified number of members randomly selected from said data set;

evaluating each of said plurality of subsets against a set of reliable measurement results for said subject;

selecting one of said subsets based on a preselected set of criteria related to reliable measurement results; and using said selected set to form an optimal calibration for said device to said subject.

2. The method of claim 1 wherein the step of forming cross-products further comprises forming second and third order terms.

3. The method of claim 1 wherein the step of forming a plurality of subsets further comprises the forming of subsets having at least one alternative specified number of members, said alternative number(s) unequal to said first number.

4. The method of claim 3 wherein the step of selecting one of said subsets further comprises a comparison of the subsets having said first number of members with the subsets having said alternative number(s) of members.

5. The method of claim 1 wherein the step of selecting one of said subsets further comprises performing a cross validation study for at least one subset.

6. The method of claim 1, wherein said device measures blood glucose levels in said subject.

7. The method of claim 1 wherein said set of reliable measurement results for said subject are taken from more than one of said subject's fingers.

8. The method of claim 7 wherein said set of reliable measurement results is amended by duplicating, at least once, the measurement results taken from any one of three of said subject's fingers.

9. The method of claim 1 wherein said set of reliable measurement results is amended by duplicating, at least once, at least one of the measurement results to produce at least one alternative calibration.

10. The method of claim 9 wherein said set of reliable measurement results are divided into at least one range of values.

11. The method of claim 10 wherein said set of reliable measurement results is divided into a low range, a high range, and middle range.

12. The method of claim 11 wherein each of said low, high and middle ranges is further divided into smaller ranges.

13. The method of claim 11 wherein said device measures blood glucose levels in said subject and wherein said set of reliable measurement results is divided into ranges below 120 mg/dL, greater than 240 mg/dL, and between 120 and 240 mg/dL.

14. The method of claim 10 wherein the step of using said selected set to form an optimal calibration further comprising using one of said alternative calibrations over each of said ranges of values.

15. The method of claim 1 wherein said data set further comprises non-optical data terms.

16. A method for calibrating a non-invasive NIR blood glucose measurement device to a subject, said method comprising the steps of:

forming a data set comprising a plurality of optical measurement data terms for said NIR measurement device;

augmenting said data set by forming cross-products terms using said data terms;

forming a plurality of subsets having at least one specified number of members randomly selected from said data set;

evaluating each of said plurality of subsets against a set of reliable blood glucose measurements for said subject;

selecting one of said sets based on a preselected set of criteria, including the ability of the subset to predict said set of reliable blood glucose measurements for said subject; and using said selected set to calibrate said NIR blood glucose measurement device to said subject.

17. A non-invasive device for measuring blood glucose levels in a subject, said device comprising:

means for gathering a plurality of data terms using NIR energy;

means for storing said plurality of data terms in a data set;

means for augmenting said data set with at least one cross-product term formed from said data terms and;

means for forming a plurality of subsets from said data set;

means for evaluating each of said plurality of subsets against reliable blood glucose level measurements for said subject; and means for selecting at least one of said subsets to calibrate said device to said subject.

* * * * *